US006790450B1

(12) United States Patent
Cowden et al.

(10) Patent No.: US 6,790,450 B1
(45) Date of Patent: Sep. 14, 2004

(54) USE OF COXIELLA BACTERIA TO TREAT AUTOIMMUNE DISEASE

(75) Inventors: William Butler Cowden, Kambah (AU); Kevin John Lafferty, Curtin (AU); Lawrence Scott Gazda, Hawker (AU)

(73) Assignee: The Australian National University, Acton (AU)

( * ) Notice: Subject to any disclaimer, the term of this patent is extended or adjusted under 35 U.S.C. 154(b) by 0 days.

(21) Appl. No.: 09/142,597

(22) PCT Filed: Feb. 14, 1997

(86) PCT No.: PCT/UA97/00161

§ 371 (c)(1), (2), (4) Date: Mar. 5, 1999

(87) PCT Pub. No.: WO97/33614

PCT Pub. Date: Sep. 18, 1997

(30) Foreign Application Priority Data

Mar. 14, 1996 (AU) .............................................. PN8703

(51) Int. Cl.[7] ........................ A61K 39/02; A61K 45/00; A61K 39/395; A01N 63/00

(52) U.S. Cl. ............................... 424/234.1; 424/236.1; 424/282.1; 424/278.1; 424/93.4; 424/810; 514/866; 514/2

(58) Field of Search ........................... 424/282.1, 234.1, 424/9.2, 184.1, 236.1, 278.1, 93.1, 93.4, 810; 514/866, 814, 838, 903, 2; 530/820, 825, 350, 300

(56) References Cited

U.S. PATENT DOCUMENTS 6,066,333 A * 5/2000 Willis et al. ................ 424/464

FOREIGN PATENT DOCUMENTS

WO WO 87/06590 * 11/1987

OTHER PUBLICATIONS

Williams et al. Infect. Immun. 51:851–858, 1986.*
van Eden et al. Nature 331: 171–173, 1988.*
Jindal et al. Mol. Cell. Biol. 9: 2279–2283, 1989.*
Lamb et al. Mol. Biol. Med. 7: 311–321, 1990.*
van Eden et al. Rheumatol. Int. 9: 187–191, 1989.*
Qin et al. J. Immunol.150: 2072–2080, 1993.*
Vodkin et al. J. Bacteriol. 170: 1227–1234, 1988.*
Edgington. Biotechnology 13: 1442–1444, Dec. 13, 1995.*
Zhang et al. Acta Virologica 38: 327–332, 1994.*
Gajdosova et al. Acta Virologica 38: 339–344, 1994.*
Levy et al. Eur. J. Epidemiol. 5: 447–453, abstract, 1989.*
Roue et al. Lancet 341: 1094–1095, abstract, 1993.*
Ackland et al. Med. J. Austral. 160: 704–708, 1994.*
Stchepinsky et al. Arch. Mal. Coeur. Viass. 88: 511–515, Apr., abstract, 1995.*
Kayser et al. Respiration 62: 114–116, Mar., 1995.*
Tobin et al. Am. J. Med. 72: 396–400, 1982.*
Elias et al. PNAS 87: 1576–1580, 1990.*
Toyota et al. Diabetes 35: 496–499, 1993.*

Atkinson et al., "Are Insulin Autoantibodies Markers for Insulin–Dependent Diabetes Mellitus?," *Diabetes* 35:894–898, Aug. 1986.

Bach, "Insulin–Dependent Diabetes Mellitus as an Autoimmune Disease," *Endocrine Reviews* 15(4):516–542, 1994.

Bowen et al., "Successful Allotransplantation of Mouse Pancreatic Islets to Nonimmunosuppressed Recipients," *Diabetes* 29(suppl. 1):98–104, Feb. 1980.

Davis et al., "The Role of Polymorphic I–$A^k$ β Chain Residues in Presentation of a Peptide from Myelin Basic Protein," *J. Exp. Med* 169:2239–2244, Jun. 1989.

Gross et al., "Prevention of Diabetes Mellitus in Non–Obese Diabetic Mice by Linomide, a Novel Immunomodulating Drug," *Diabetologia* 37:1195–1201, 1994.

Harada et al., "Prevention of Overt Diabetes and Insulitis in NOD Mice by a Single BCG Vaccination," *Diabetes Research and Clinical Practice* 8:85–89, 1990.

Honeyman and Harrison, "The Innumologic Insult in Type 1 Diabetes," *Springer Seminars in Immunopathology* 14:253–274, 1993.

Kanazawa et al., "Non–Obese–Diabetic Mice: Immune Mechanisms of Pancreatic β–Cell Destruction," *Diabetologia* 27:113–115, 1984.

Lakey et al, "Prevention of Recurrence of Insulin–Dependent Diabetes Mellitus in Islet Cell–Transplanted Diabetic NOD Mice Using Adjuvant Therapy," *Transplantation Proceedings* 24(6):2848, Dec. 1992.

Lakey et al, "BCG Immunotherapy Prevents Recurrence of Diabetes in Islet Grafts Transplanted into Spontaneously Diabetic NOD Mice," *Transplantation* 57(8):1213–1217, Apr. 1994.

Makino et al., "Breeding of a Non–Obese, Diabetic Strain of Mice," *Exp. Anim.* 29(1):1–13, 1980.

McInerney et al., "Prevention of Insulitis and Diabetes Onset by Treatment With Complete Freund's Adjuvant in NOD Mice," *Diabetes* 40:715–725, Jun. 1991.

Qin et al., "Mechanisms of Complete Freund's Adjuvant Protection Against Diabetes in BB Rats: Induction of Non–Specific Suppressor Cells," *Autoimmunity* 12:193–199, 1992.

(List continued on next page.)

*Primary Examiner*—S. Devi
(74) *Attorney, Agent, or Firm*—Seed Intellectual Property Law Group PLLC

(57) ABSTRACT

Therapeutic compositions including a species of Coxiella or one or more antigenic components therefrom or analogous or homologous components thereof are disclosed. These compositions are useful in preventing, inhibiting, delaying onset of or otherwise ameliorating the effects of an autoimmune disease in a mammal, particularly insulin-dependent diabetes mellitus (IDDM). They arm also useful in prolonging survival of islet tissue transplanted into a mammal.

6 Claims, 2 Drawing Sheets

OTHER PUBLICATIONS

Sadelain et al., "Prevention of Type I Diabetes in NOD Mice by Adjuvant Immunotherapy," *Diabetes* 39:583–589, May 1990.

Sadelain et al., "Prevention of Diabetes in the BB Rat by Early Immunotherapy Using Freund's Adjuvant" *Journal of Autoimmunity* 3(6):671–680, Dec. 1990.

Shehadeh et al., "Altered Cytokine Activity in Adjuvant Inhibition of Autoimmune Diabetes," *J. Autoimmunity* 6(2):291–300, Apr. 1993.

Ulaeto et al., "A T–Cell Dormant State in the Autoimmune Process of Nonobese Diabetic Mice Treated with Complete Freund's Adjuvant," *Proc. Natl. Acad. Sci.* (*USA*). 89(9):3927–3931, May 1992.

Wang, et al., "Prevention of Recurrence of IDDM in Islet–Transplanted Diabetic NOD Mice by Adjuvant Immunotherapy," *Diabetes* 41(1):114–117, Jan. 1992.

Yagi et al., "Possible Mechanism of the Preventive Effect of BCG Against Diabetes Mellitus in NOD Mouse: II. Suppression of Pathogenesis by Macrophage Transfer from BCG–Vaccinated Mice," *Cellular Immunology* 138(1):142–149, 1991.

* cited by examiner

USE OF COXIELLA BACTERIA TO TREAT AUTOIMMUNE DISEASE

TECHNICAL FIELD

The present invention relates generally to a method for ameliorating the adverse effects of autoimmune conditions and to therapeutic conditions useful for same. More particularly, the present invention provides a method for the prophylaxis and/or treatment of insulin-dependent diabetes mellitus (IDDM) by preventing, inhibiting, delaying onset of, or otherwise ameliorating the effects of the disease. The present invention further provides a method for the prophylaxis and/or treatment of pancreatic beta cell destruction in islet tissue transplanted into recipients. The present invention also provides therapeutic compositions useful in the prophylaxis and/or treatment of IDDM and pancreatic beta cell destruction.

BACKGROUND OF THE INVENTION

IDDM is a debilitating, chronic cell mediated autoimmune disease characterised by lymphocytic infiltration of the pancreatic islets and lymphocyte mediated destruction of insulin-producing beta-cells (Bach 1994, Honeymoon and Harrison, 1993) and is defined by the presence of hyperglycemia. Type 1 diabetes, or IDDM, occurs where an individual's own immune system destroys the cells responsible for insulin production; the beta cells residing in the islets of Langerhans of the pancreas. IDDM in humans, in the non-obese diabetic mouse (NOD mouse [Makino et al, 1980; Kanazawa et al, 1984]) and in the BB rat is an autoimmune disease associated with the development of auto-antibodies reactive to islet-associated antigens (Atkinson et al., 1986). Susceptibility to the development of disease both in humans and in non-human animals is under genetic control. Genes of the major histocompatibility complex (MHC), specifically those found in the class II MHC region, which control structures involved in the presentation of antigen to the cellular components of the immune system are to a large extent responsible for the disease-prone status (Davis et al., 1989).

In animal models, a single immunostimulation with live, infectious BCG (*Mycobacterium bovis*; Bacille Calmette-Guérin) vaccination (Yagi et al., 1991) or powerful immunoadjuvants based on heat-killed Mycobacterium tuberculosis (or *Mycobacterium butyricum*) either early or late in the disease process, can largely suppress the development or progression of disease respectively (reviewed in Bach, 1994). Freund's Complete Adjuvant (FCA) [often referred to as complete Freund's adjuvant or CFA], which consists of a suspension of heat-killed M. tuberculosis (or *M. butyricum*) in mineral oil together with a surfactant is considered to be a particularly powerful immunological adjuvant. Immunostimulation with a single injection of FCA has been shown to substantially protect both NOD mice (Sadelain et al., 1990a; McInerney et al., 1991) and BB rats (Sadelain et al., 1990b) from developing diabetes.

Immuno-adjuvants such as bacterial lipopolysaccharide (LPS) or muramyl dipeptide (MDP) which are not based upon either live or heat-killed Mycobacterium sp. are not effective in preventing diabetes.

Another biological response modifier, OK-432, prepared from streptococci, when administered to NOD mice, has been shown to prevent the onset of diabetes until mice reach 24 weeks of age (Toyota et al., 1986); no information exists showing whether or not these animals remain free of diabetes once the therapy is discontinued. It has also been shown that the immunomodulating drug quinoline-3-carboxamide (Linomide) when given continuously in the drinking water to NOD mice, starting at a young age (5 weeks), will block the onset of diabetes until the mice are at least 40 weeks old (Gross et al., 1994). However, this agent is not as effective when therapy is started on mice which are 16 weeks old; in this case the cumulative incidence of diabetes is 28% by the time the mice are 42 weeks old even though the drug is given on a continuous basis (Gross et al., 1994).

FCA appears to induce cell-mediated protection against development of diabetes. It has, for example, been shown that spleen cells taken from NOD mice, which had been treated with FCA, were capable of suppressing the response of co-cultured control syngeneic spleen cells to mitogens (Sadelain et al., 1990a; McInerney et al., 1991). When spleen cells are taken from BCG vaccinated NOD mice and passaged into naive NOD mice, the latter are protected from developing diabetes (Harada et al., 1990; Yagi et al., 1991). The same effect has been observed in FCA-treated BB rats (Qin et al., 1992). It should be noted that others have found FCA to be less effective than BCG in transferring protection in this manner (Qin et al., 1993; Ulaeto et al., 1992).

Recurrence of disease in grafted tissue is a major factor which interferes with the transplantation of pancreatic islets into spontaneously diabetic NOD mice. Currently it is not possible to successfully transplant islets into animus that have developed disease hi spontaneously without recourse to extensive immunosuppression (Wang et al., 1991). Recurrence of disease can, however, be blocked in spontaneously diabetic NOD mice if they are treated with FCA (Wang et al., 1992; Lakey et al., 1992) or BCG (Lakey et al., 1994) prior to transplantation.

Immunostimulation of NOD mice by either BCG or FCA does not totally block the autoimmune response, instead the response is converted from a destructive into a non-destructive form of auto-immunity (Shehadeh et al., 1993). Thus, functionally these agents do not prevent or reverse autoimmunity directed against islet tissue, although they do prevent development of insulin-dependent diabetes.

It would appear, therefore, that deviation of the immune response away from destructive autoimmunity by immunostimulation could offer a benign approach to the prevention of diabetes and the development of more effective means for the transplantation of islets in the case of existing disease.

However, neither FCA nor BCG is an ideal therapeutic agent for preventing the development, of IDDM. Despite the fact that FCA is a very powerful immuno-adjuvant, it has not found wide-spread use outside the laboratory because of the adverse tissue reaction (severe ulceration) it provokes in mammals. In most countries, FCA is banned from veterinary use and, of course, it cannot be used in humans. BCG is an infectious agent which cannot be given to certain individuals, especially those who are immunosuppressed.

SUMMARY OF THE INVENTION

In work leading to the present invention, the inventors sought to develop agents capable of blocking the development of IDDM in humans which are sufficiently benign for general use and most effective in terms of deviating the immune response away from destructive autoimmunity.

Accordingly, one aspect of the present invention contemplates a method for preventing, inhibiting, delaying onset of or otherwise ameliorating the effects of an autoimmune disease in a mammal, said method comprising administering to said mammal an autoimmune-preventing effective amount of a species of Coxiella or one or more antigenic components therefrom or analogous or homologous components thereof.

Another aspect of the present invention provides a method for prolonging survival of islet tissue transplanted into a mammal, said method comprising administering into said mammal an effective amount of a species of Coxiella or one or more antigenic components therefrom or analogous or homologous components thereof.

Still a further aspect of the present invention is directed to a therapeutic composition for use in preventing, inhibiting, delaying onset of or otherwise ameliorating the effects of an autoimmune disease in a mammal said composition comprising a species of Coxiella or one or more antigenic components therefrom or analogous or homologous components thereof and one or more pharmaceutically acceptable carriers and/or diluents.

Yet still another aspect of the present invention relates to the use of a species of Coxiella or one or more antigenic components therefrom or analogous or homologous components thereof in the manufacture of a medicament for the treatment of an autoimmune disease in a mammal.

DETAILED DESCRIPTION

Figure 1:
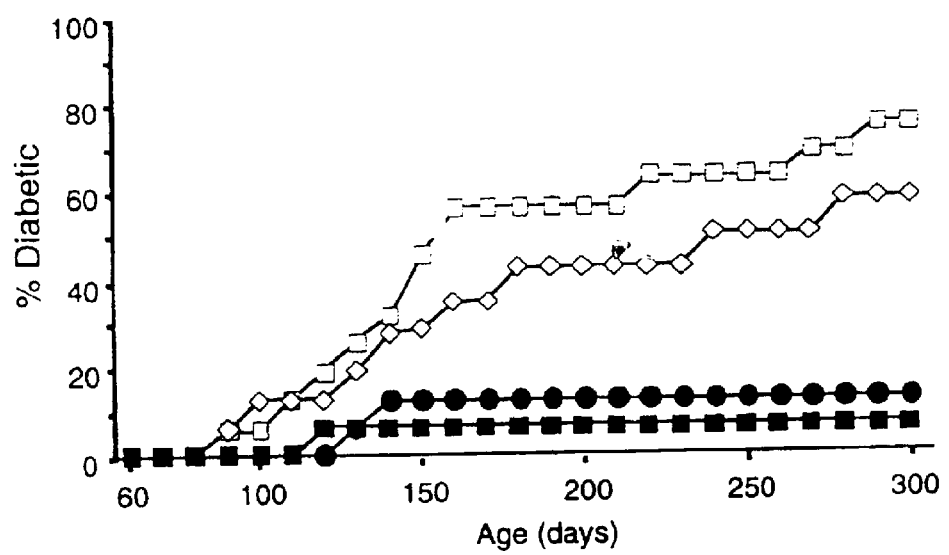

Coxiella is a genus of Gram negative bacteria of the Rickettsieae. The only known species to date is *Coxiella burnetii* which is the causative agent of Q fever in man. Reference herein to "Coxiella" species, therefore includes *C. burnetii* or an organism related thereto at the functional level. The present invention requires that the Coxiella species be attenuated, killed or otherwise rendered non-infectious prior to use.

The use of non-infectious agents in the prophylaxis and/or treatment of autoimmune disease conditions offers a major advantage in clinical terms. Infectious agents, even those such as BCG, frequently pose a problem if administered to an immunocompromised individual and, while FCA might be effective in humans, its use is precluded by the severe ulcerative skin lesions which develop following its use. In accordance with the present invention, an ideal agent would be capable of blocking the induction of the autoimmune disease as well as inhibiting disease recurrence in transplanted islet tissue in diabetic patients.

The present invention is particularly directed and exemplified with reference to IDDM as the autoimmune disease. This is done, however, with the understanding that the present invention extends to a range of autoimmune conditions and in particular, autoimmune conditions which can be treated by deviating an immune response away from destructive autoimmunity. Examples of autoimmune conditions contemplated herein other than IDDM include but are not limited to pernicious anaemia, autoimmune chronic hepatitis, ulcerative colitis, primary biliary cirrhosis multiple sclerosis and systemic lupus erythematosis (SLE).

According to a preferred embodiment, the present invention contemplates a method of preventing, inhibiting, delaying onset of or otherwise ameliorating the effects of IDDM in a mammal, said method comprising administering to said mammal an autoimmune-preventing effective amount of a species of Coxiella or one or more antigenic components therefrom or analogous or homologous components thereof.

The present invention extends to the prophylaxis or treatment of any mammal such as but not limited to a human, primate, livestock animal (eg. sheep, cow, horse, pig, donkey), companion animal (eg. dog, cat), laboratory test animal (eg. mouse, rat, guinea pig, rabbit, hamster) or captive wild animal (eg. fox, deer, kangaroo).

Accordingly, a preferred aspect of the present invention is directed to a method of preventing, inhibiting, delaying onset of or otherwise ameliorating the effects of IDDM in a human, said method comprising administering to said mammal an autoimmune-preventing effective amount of a species of Coxiella or one or more antigenic components therefrom or analogous or homologous components thereof.

The present invention particularly relates to *C. burnetii* or a related organism or an antigenic component thereof or an analogous or homologous component thereof. A particularly useful form of *C. burnetii* is a killed preparation of the bacterium such as a heat killed or formulin killed preparation. One such useful form is QVAX which is a Q fever vaccine or Q fever complement fixing antigen phase I (QFA) [both available from CSL Limited, Melbourne, Australia]. The present invention extends however to live, attenuated strains of *C. burnetii* or to preparations of the bacterium killed or rendered non-infectious by other means.

The present invention further contemplates antigenic components of *C. burnetii* such as a lysed preparation of the whole organism, a membrane,wall preparation, an endospore preparation or one or more purified or partially purified antigenic molecules therefrom or analogous or homologous components thereof.

Accordingly, a particularly preferred embodiment of the present invention is directed to a method for preventing, inhibiting, delaying onset of or otherwise ameliorating the effects of IDDM or pancreatic beta cell destruction in islet tissue transplantation recipients in a human, said method comprising administering to said human, an effective amount of killed or attenuated *C. burnetii* or an antigenic component thereof or analogous or homologous components thereof.

Preferably, QVAX or QFA is administered.

Generally, administration is for a time and under conditions sufficient for the immune response to deviate from a destructive immune response to a non-destructive immune response.

This and other aspects of the present invention are predicted in part of the surprising result that a Q fever antigen (*C. burnetii*), and in particular killed *C. burnetii* in the form of, for example, QFA or QVAX when injected into NOD mice inhibits diabetes in a high percentage ($\geq 90\%$) of treated mice. The agents of the present invention are not recognised immuno-adjuvants and yet are as effective as either BCG or FCA in preventing the development of diabetes in NOD mice.

The present invention contemplates Coxiella sp and in particular *C. burnetii* and antigenic components thereof as well as recombinant or synthetic forms of the antigenic components and analogues or homologues thereof from another source. The latter molecules may be identified, for example, by natural product screening of coral, ocean beds, plants, soil and other microorganisms. These molecules may structurally mimic the antigenic components from *C. burnetii* or may only functionally mimic these components by preventing, inhibiting, delaying onset of, curing or otherwise ameliorating the effects of an autoimmune disease and in particular IDDM. One convenient way of screening for analogues or homologues is via anti-idiotypic antibody screening. For example, antibodies are raised to particular antigenic components of *C. burnetii* and anti-idiotypic antibodies raised to the first mentioned antibodies. The anti-idiotypic antibodies are then used to screen for molecules capable of binding or otherwise interacting with these antibodies.

Alternatively, chemical analogues may be made from isolated antigenic components of C. burnetii or from analogous or homologous components thereof.

Analogues of C. burnetii antigenic components contemplated herein include, but are not limited to, where the antigenic component is proteinaceous, modifications to side chains, incorporation of unnatural amino acids and/or their derivatives during peptide, polypeptide or protein synthesis and the use of crosslinkers and other methods which impose conformational constraints on the proteinaceous molecule or their analogues. Such analogues are particularly useful if they are more stable when used for administration in a vaccine formulation.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_{60}$ and $N_{60}$-methylamino acids, introduction of double bonds between $C_{60}$ and $C_{62}$ atoms of amino acids and the formation of cyclic peptides or analogues by introducing covalent bonds such as forming an amide bond between the N and C termini, between two side chains or between a side chain and the N or C terminus.

The present invention further contemplates chemical analogues of C. burnetii antigenic components capable of acting as antagonists or agonists of same or which can act as functional analogues of the antigenic components. Chemical analogues may not necessarily be derived from C. burnetii molecule but may share certain conformational similarities. Alternatively, chemical analogues may be specifically designed to mimic certain physiochemical properties of the antigenic components. Chemical analogues may be chemically synthesised or may be detected following, for example, natural product screening.

Antagonists may be important molecules to control the extent of immunostimulation or to prevent unwanted immune responses such as hypersensitivity reactions. Agonists may be important to enhance immunostimulatory properties.

TABLE 1

| Non-conventional amino acid | Code |
| --- | --- |
| α-aminobutyric acid | Abu |
| α-amino-α-methylbutyrate | Mgabu |
| aminocyclopropanecarboxylate | Cpro |
| aminoisobutyric acid | Aib |
| aminonorbornylcarboxylate cyclohexylalanine | Norb |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |

TABLE 1-continued

| Non-conventional amino acid | Code |
| --- | --- |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dmngln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenylethylamino)cyclopropane | Nmbe |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methytglutamic acid | Nmglu |
| Chexa L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methytethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |

In a preferred embodiment of the present invention, the human targeted for therapy would be known to be likely to develop IDDM or is a patient who has recently been diagnosed to be in the early stages of IDDM or is a patient suffering from IDDM and who could be transplanted with islet tissue from a non-diabetic donor. The human may also be an "at risk" individual due to certain environmental conditions or may have a genetic propensity to develop IDDM such as due to a family history of the disease.

Another aspect of the present invention contemplates a method for prolonging survival of islet tissue transplanted into a human, said method comprising administering into said mammal an effective amount of a species of *C. burnetii* or one or more antigenic components therefrom or analogous or homologous components thereof.

Yet another aspect of the present invention provides a therapeutic composition for use in preventing, inhibiting, delaying onset of or otherwise ameliorating the effects of an autoimmune disease in a mammal said composition comprising a species of Coxiella or one or more antigenic components therefrom or analogous or homologous components thereof and one or more pharmaceutically acceptable carriers and/or diluents.

Preferably, the mammal is a human. Preferably the autoimmune condition is IDDM or pancreatic beta cell destruction in islet tissue of transplantation recipients. Preferably the Coxiella species is *C. burnetii* or an antigenic component or an analogous or homologous component thereof or is a killed or otherwise non-infectious in attenuated form of the bacterium. Most preferably, the administered agent is QFA or QVAX or functionally equivalent forms thereof.

The term "active component" is hereinafter used to refer to a Coxiella species and in particular *C. burnetii* or to antigenic components therefrom or analogous or homologous components thereof.

The active component is administered in therapeutically effective amounts. A therapeutically effective amount means that amount necessary at least partly to attain the desired effect, or to inhibit or delay the onset of, inhibit the progression of, or halt or prevent altogether, the onset or progression of the particular condition being treated such as IDDM. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

The formulation of such therapeutic compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Phamnaceutical Sciences*, 18th Edition, Mack Publishing Company, Pa., USA. Except insofar as any conventional media or agent is incompatible with the active ingredient, use thereof in the pharmaceutical compositions of the present invention is contemplated.

Therapeutic formulations suitable for injectable use include sterile aqueous solutions (where water soluble) or dispersions and sterile powders for the extemporaneous preparation of sterile injectable solutions or dispersions. The present invention also contemplates administration via topically applied compositions where active components may be modified to permit entry via the skin. It must be stable under the conditions of manufacture and storage and must be preserved against the contaminating action of microorganisms such as bacteria and fungi.

The carrier can be a solvent or dispersion medium containing, for example, water, ethanol, polyol (for example, glycerol, propylene glycol and liquid polyethylene glycol and the like), suitable mixtures thereof and vegetable oils. The proper fluidity can be maintained, for example, by the use of a coating such as licithin, by the maintenance of the required particle size in the case of dispersion and by the use of surfactants. The preventions of the action of microorganisms can be brought about by various antibacterial and antifungal agents, for example, parabens, chilorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active components in the required amount in the appropriate solvent with various of the other ingredients enumerated above. Generally, dispersions are prepared by incorporating the various active components, sterilized where appropriate, into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient.

Preferred compositions or preparations according to the present invention contains between about 0.1 $\mu$g and about 2000 mg of active component. Other ranges contemplated herein include from about 1 $\mu$g to about 1000 mg, from about 10 $\mu$g to about 100 mg and from about 100 $\mu$g to about 50 mg. Where killed or attenuated or otherwise non-infectious organisms are administered, a suitable range is from about $10^2$ to about $10^6$ cells/ml of therapeutic composition being administered to a patient. The present invention also contemplates amounts outside this range, the important feature being an amount which is effective to induce a deviation from destructive autoimmunity to a non-destructive form of autoimmunity.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active component, use thereof in the therapeutic compositions is contemplated. Supplementary active components can also be incorporated into the compositions. Examples of supplementary components include various cytokines, insulin, antibacterial agents and immune potentiating molecules.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active component is compounded for convenient and effective administration in effective amounts with a suitable pharmaceutically acceptable carrier in dosage unit form as hereinbefore disclosed. A unit dosage form can, for example, contain the principal active component in amounts ranging from about 0.1 $\mu$g to about 2000 mg. Expressed in proportions, the active component is generally present in from about 0.5 $\mu$g to about 2000 mg/ml of carrier. Expressed in cellular terms, the unit dosage may range from $10^2$ to $10^{16}$ cells/ml of carrier of diluent. In the case of compositions containing supplementary active component, the dosages are determined by reference to the usual dose and manner of administration of the said components. The present invention also contemplates dosage ranges outside these amounts.

The active components of the present invention may be administered alone or in combination with other therapeutic molecules such as molecules which reduce effects of the autoimmune pathology associated with IDDM. A single dose may be administered and is preferred although multiple doses may be required with intervals of from minutes to hours, days to weeks or months to years.

Reference herein to "preventing" IDDM includes total prevention of IDDM or substantial prevention for a limited time or even substantially indefinitely or delaying onset of IDDM or reducing the severity or otherwise ameliorating the effects of IDDM. For example, in humans, prevention includes but is not limited to delaying onset for from 1 to 60 years or from 2 to 30 years or from 3 to 15 years. As a test system for prevention in mice may range from weeks to years.

Figure 2:
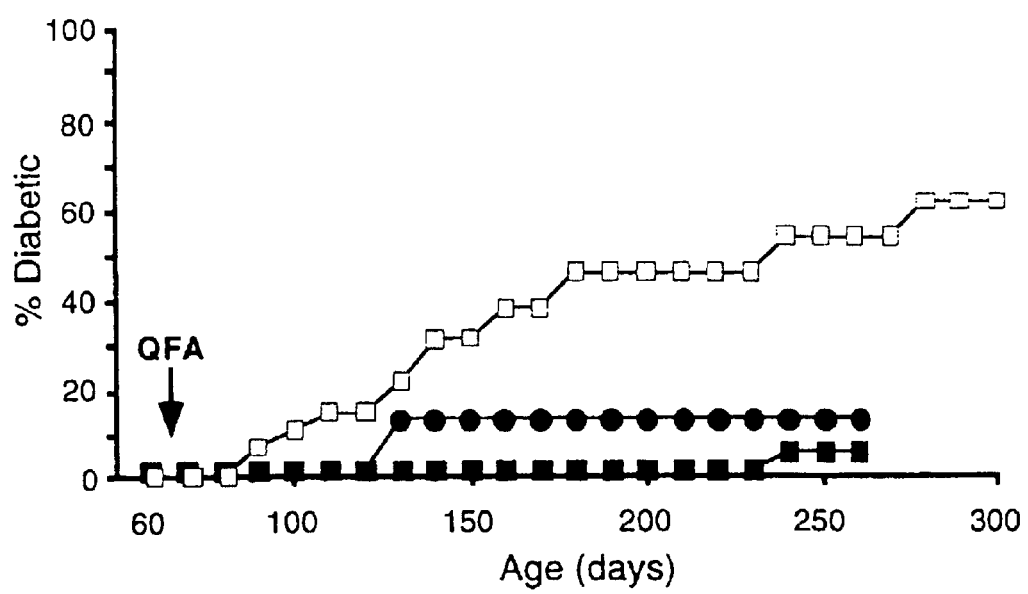

It has been shown that the active components of the present invention including one or more Q fever antigens and in particular killed *C. burnetii* are more efficacious than either FCA or BCG in protecting beta cells from autoimmune destruction in NOD mice. Thus, NOD mice treated with doses of either FCA, BCG or Q fever antigen(s), did not develop IDDM. Significantly, more viable beta cells were found in the pancreases of mice which had been treated with the active components than in the mice treated with either FCA or BCG.

NOD female mice between 120 and 180 days of age, which had become diabetic spontaneously, treated with an active component of the present invention and then transplanted with syngeneic islet tissue essentially as described in Bowen et al, (1980), maintained normal blood glucose levels. Control mice, treated with saline instead of an active component and then similarly transplanted with syngeneic islet tissue, become diabetic, for example within about 10 days of tissue transplantation. Histological sections of transplanted tissue taken from the saline treated group, at the time they become diabetic, show a massive inflammatory infiltrate into the transplanted tissue, with essentially complete beta cell destruction. Histological sections taken for example one month after treatment from the animals treated with an active component show little or no inflammatory infiltrate and the beta cells are intact.

The present invention is further described by reference to the following non-limiting Figures and Examples. It is to be understood, however, that the Examples are included solely for the purposes of exemplifying the present invention, and should not be understood in any way as a restriction on the broader aspects of the subject invention as set out above.

In the Figures:

FIG. 1 is a graphical representation showing the prevention of IDDM in NOD mice following administration of QFA:

□ Saline (12/16 diabetic)

◇ Saline (8/13 diabetic)

● FCA (2/17 diabetic)

■ QFA 200 μl (1/14 diabetic)

FIG. 2 is a graphical representation showing the prevention of IDDM in NOD mice following administration of QFA:

□ Saline (8/13 diabetic)

QFA 70 μl (2/15 diabetic)

■ QFA 200 μl (1/14 diabetic)

In the following examples, all specific pathogen-free NOD mice were obtained from the Animal Breeding Establishment, The Australian National University, Canberra, ACT, Australia. Mice were housed under specific pathogen-free conditions with sterilised micro-isolator cages and bedding. Sterilised food and water were provided ad libitum. Cages were changed in laminar flow hoods using sterile technique by a laboratory assistant who was dedicated solely to this task and who was not responsible for the maintenance of any other animals. Cages were housed in hepa filtered ventilation racks with a 12 hour day night cycle. Routine serological monitoring was performed by the Murine Virus Monitoring Service, (Primary Industries, Adelaide, South Australia), for evidence of infection by any of 15 different murine viruses. Since the implementation of this procedure, the NOD mouse colony used in this study has tested negative for all of these viruses.

EXAMPLES

Example 1

This example demonstrates the effectiveness of a single 200 μl dose of Q fever complement fixing antigen Phase I (QFA) in inhibiting the occurrence of IDDM in NOD mice.

Female NOD littermates between 64 and 69 days of age were divided into two groups and injected intraperitoneally (ip) with either 200 μl of Q fever complement fixing antigen phase I (obtained from CSL, Melbourne Australia) or 200 μl of saline solution. Fifteen mice were injected with QFA while 14 littermates received saline solution. One animal from each group was found dead of unknown causes during the course of the experiment.

For comparison, in a similar manner, 17 female NOD littermates between the ages of 64 and 85 days of age were injected in the right rear footpad with 50 Al complete Freund's adjuvant (FCA) (Bacto lot # 784560) given as an emulsion in an equal volume of normal saline; 16 littermates received saline solution only.

Mice in all of the four groups were checked three times per week for elevated glucose concentrations in their urine (Tes-Tape, Eli Lilly and Co, Indianapolis, Ind., USA). When mice were found to have raised urinary glucose levels, whole blood glucose levels were determined with a Companion 2 Sensor (Medisense, Cambridge, Mass., USA), Where two consecutive daily blood glucose readings above the 95% confidence interval for NOD mice in this colony (3.9–9.1 mmol/L) were obtained, the animal was deemed to be diabetic. Animals were monitored until they reached 300 days of age or became diabetic. The results of this experiment are shown in FIG. 1.

As indicated in FIG. 1, at 300 days of age, 2 out of 17 mice (12%) in the FCA treated group had become diabetic while 12 out of 16 mice (75%) of their saline treated littermates became diabetic. At 300 days of age only 1 out of 14 (7%) of the QFA treated mice had developed diabetes compared to 8 out of 13 (62%) of their saline treated littermates.

Example 2

This example demonstrates the effectiveness of single 20 or 70 μl doses of QFA in inhibiting the occurrence of IDDM in NOD mice.

Female NOD mice between 62 and 72 days of age were injected intraperitoneally (ip) with either 70 Sol of QFA or 20 μl of QFA. Fifteen mice were injected with 70 μl of QFA and 15 mice received 20 μl QFA. One animal from the 20 μl group was found dead of unknown causes during the course of the experiment. The 200 μl saline injected group of female NOD mice from Example 1 served as control animals. Mice were checked three times a week for elevated glucose levels in their urine (Tes-Tape, Eli Lilly and Co, Indianapolis, Ind., USA). When positive for urinary glucose, whole blood glucose levels were determined with a Companion 2 sensor (Medisense, Cambridge, Mass., USA). Where two consecutive daily blood glucose readings above the 95% confidence interval for NOD mice in this colony (3.9–9.1 mmol/L) were obtained, the animal was deemed to be diabetic. The animals were monitored until they reached 260 days of age or became diabetic. The results of this experiment are shown in FIG. 2. At 260 days of age only 2 out of 15 (13%) of the group treated with 70 μl of QFA and 1 out of 14 (7%) of the 20 μl QFA treated group had become diabetic, compared to 8 out of 13 (62%) of the saline treated NOD mice from Example 1 that served as controls for this experiment.

Example 3

This example demonstrates that QFA is more efficacious than either FCA or BCG in protecting beta cells from autoimmune destruction in NOD mice.

A group of 10 specific pathogen-free, 61–66 day old female NOD mice were injected in both rear footpads with 40 μl (total dose 80 μl) reconstituted freeze-dried live BCG (Pasteur Merieux, Lyon, France). A second group of 17, 64–85 day old female NOD animals, were injected with FCA emulsified with an equal volume of normal saline (50 μl in right hind footpad). A third group of 14 age-matched female NOD mice were injected, ip, with 200 μl of QFA. Two additional groups of 14 age-matched female NOD mice received either 70 or 20 μl of QFA, ip. When the mice had reached 300 days of age, 10, 13 and 11 mice from the BCG, FCA and each of the QFA treated groups respectively (all nondiabetic) were sacrificed by cervical dislocation and their pancreases removed for histological sectioning and examination. Thirteen age-matched nondiabetic female NODs were also sacrificed arid their pancreases similarly examined. Pancreases were fixed in 10% v/v neutral buffered formalin for 18 hours. Immunohistochemistry was used to stain for the presence of insulin and glucagon positive islets (DAKO Corporation, Carpinteria, Calif.). Serial 5 μm sections were stained for either insulin or glucagon and examined by light microscopy. As shown in Table 1 only 16% of islets in the BCG treated group stained positive for insulin production, 52% of islets in the FCA treated group stained positive for insulin and in the QFA treated group 87%, 77% and 75% of islets stained positive for insulin production in the 200, 70 and 20 μl treatment groups respectively. Seventy-three percent of the islets examined from pancreases of age-matched female nondiabetic NOD mice had insulin positive islets while 27% of the islets were positive for glucagon only.

TABLE 1

| Treatment | % Insulin positive islets* | % Collapsed Islets* (Glucagon only) |
|---|---|---|
| BCG | 16 (11/69) | 84 (58/69) |
| FCA | 52 (31/60) | 48 (29/60) |
| QFA (200 μl) | 87 (105/121) | 13 (16/121) |
| QFA (70 μl) | 77 (40/52) | 23 (12/52) |
| QFA (20 μl) | 75 (41/55) | 25 (14/55) |
| Age matched females | 73 (22/30) | 27 (8/30) |

*Figures in parentheses represent the number of positive or collapsed islets/total number examined.

Example 4

This example demonstrates the effectiveness of Q fever antigen treatment in preventing the recurrence of IDDM in spontaneously diabetic NOD mice transplanted with syngeneic islet tissue.

Donor animals, four to eight week old NOD female mice, were anaesthetised with an intraperitoneal injection of avertin solution. A curved 27 gauge needle was inserted into the common bile duct at the hilus after the distal end of the duct had been clamped. Approximately 3 ml of cold collagenase P (Boehringer Mannheim, Castle Hill, NSW, Australia) made to 2.5 mg/ml in Hanks balanced salt solution +0.05% w/v BSA was injected immediately after dissection of the intrathoracic aorta. The pancreas was then excised and digested while held stationary in a 37°C. water bath for 15 minutes and islets were hand-picked and transplanted essentially as described in Bowen et al.

Recipient mice, female NODs which had been diabetic for less than 2 weeks but for at least 3 days prior to transplantation and which had a mean blood glucose levels of 29.7±1.38 mmol/L (range 21.2–33.4 mmol/L) on the day of engraftment, following anaesthesia (avertin, i.p.), received 450 islets under the left kidney capsule in a clot of recipient blood. These animals were divided into two groups. The treatment group, n=9, received QFA, 70 μl, s.c., at the time of transplantation and the control group, n=10 received an injection of saline, 70 μl , s.c. at the time of transplantation.

Blood glucose levels were determined for all islet-engrafted mice beginning on the day following transplantation. In the majority of cases in both the treated and control groups, a few days were required for normoglycaemia to be established. All 10 untreated islet-transplanted mice were hyperglycaemic (blood glucose>22 mmol/L) by day 10 post-transplantation. Mice which were treated with QFA were largely protected against disease recurrence as evidenced by their blood glucose levels (mean blood glucose levels 8.17±0.67) on day 10 post-transplantation. Thus, in the QFA-treated islet-transplanted group 6 out of 9 mice were protected from disease recurrence for greater than 30 days. One mouse out of 9 became diabetic on day 25 post-transplantation and two mice failed to become normoglycaemic following engraftment.

Example 5

This example demonstrates that *C. burnetii* vaccine (QVAX) is effective in inhibiting the occurrence of IDDM in NOD mice.

Female NOD littermates 72 days of age were divided into two groups and injected subcutaneously with either 100 μl of QVAX (obtained from CSL, Melbourne, Australia) or 100 μl of saline solution. Ten mice were treated with QVAX while 10 littermrates received saline solution.

Mice in both groups were checked three times per week for elevated glucose concentrations in their urine (Tes-Tape, Eli Lilly and Co., Indianapolis, Ind.). When mice were found to have raised urinary glucose levels, whole blood glucose levels were determined with a Companion 2 Sensor (Medisense, Cambridge, Mass., USA). Where two consecutive daily blood glucose readings above the 95% confidence interval for NOD mice in this colony (3.9–9.1 mmol/L) were obtained, the animal was deemed to be diabetic. Animals were monitored until they reached 100 days of age or became diabetic.

None of the QVAX treated mice became diabetic during this period while 2 out of 10 of the saline treated mice became diabetic by 100 days of age. At 200 days of age, 9 out of 10 QVAX-treated mice were protected from developing diabetes while 9 out of 10 saline-treated mice developed diabetes.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Atkinson, M. A., et al *Diabetes*, 35, 894–898, 1986.
Bach, J. F., *Endocr. Rev.*, 15, 516–54, 1994.
Bowen, K. M., et al *Diabetes*, 29, 98–104, 1980.
Davis, C. B., et al *J. Exp. Med.*, 169, 2239–2244, 1989.
Gross, D. J., et al *Diabetologia*, 37, 1195–1201, 1994.
Harada, M., et al *Diabetes Res. Clin. Pract.*, 8, 85–89, 1990.

Honeyman, M. C. and Harrison, L. C. *Springer Semn. Immunopathol.*, 14, 253, 1993.

Kanazawa, Y. et al *Diabetologia.*, 27, 113–115, 1984.

Lakey, J. R., et al *Transplant. Proc.*, 24, 2848, 1992.

Lakey, J. R., et al *Transplantation*, 57, 1213–1217, 1994.

Makino S. et al *Exp. Anim.*, 29, 1–13.1980.

McInerney, M. F., et al *Diabetes*, 40, 715–725, 1991.

Qin, H. Y., *Autoimmunity*, 12, 193–199, 1992.

Quin, H. -Y., et al *J. Immunol.* 150, 2072–2080, 1993.

Sadelain, M. W. J., et al *Diabetes*, 39, 583–589, 1990a.

Sadelain, M. W. J., et al *Journal of Autoimmunity*, 3, 671–680, 1990b.

Shehadeh, N. N., et al *J. Autoimmun.*, 6, 291–300, 1993.

Toyota, T., et al *Diabetes*, 35, 496499, 1986.

Ulaeto, D., et al *Proc. Natl. Acad. Sci.* (USA). 89, 3927–3931, 1992.

Wang, T., et al *Diabetes*, 41, 114–117, 1992.

Yagi, H., et al *Cell. Immunol.*, 138, 142–149, 1991.

What is claimed is:

1. A method for use in prophylaxis or treatment of an insulin-dependent diabetes mellitus autoimmune disease in a mammal, said method comprising administering to said mammal an effective amount of an isolated non-infectious *Coxiella burnetii*.

2. The method according to claim 1 wherein the mammal is a human or laboratory test animal.

3. The method according to claim 1, wherein the insulin-dependent diabetes mellitus autoimmune disease adversely effects the survival of pancreatic islet tissue transplanted into said mammal.

4. The method according to claim 3 wherein the *C. burnetii* is in the form of a killed preparation.

5. The method according to claim 4 wherein the preparation is *C. burnetii* Q fever vaccine (QVAX).

6. The method according to claim 5 wherein the preparation is *C. burnetii* Q fever complement fixing antigen phase I (QFA).

* * * * *

UNITED STATES PATENT AND TRADEMARK OFFICE
CERTIFICATE OF CORRECTION

PATENT NO.    : 6,790,450 B1
DATED         : September 14, 2004
INVENTOR(S)   : William Butler Cowden et al.

It is certified that error appears in the above-identified patent and that said Letters Patent is hereby corrected as shown below:

Title page,
Item [22], PCT Filed, "Feb. 14, 1997" should read as -- Mar. 14, 1997 --.
Item [86], PCT No., "PCT/UA97/00161" should read as -- PCT/AU97/00161 --.

Signed and Sealed this

Twenty-seventh Day of September, 2005

JON W. DUDAS
*Director of the United States Patent and Trademark Office*